United States Patent [19]

Masuda et al.

[11] 4,297,724
[45] Oct. 27, 1981

[54] METHOD AND MACHINE FOR TRYING ON A HAIR FORM IN IMAGE

[75] Inventors: Tatsunosuke Masuda; Yoshio Ono; Seiya Sakamoto, all of Kyoto, Japan

[73] Assignees: Dainippon Screen Seizo Kabushiki Kaisha; Takara Belmont Co., Ltd., both of Japan

[21] Appl. No.: 114,947

[22] Filed: Jan. 23, 1980

[30] Foreign Application Priority Data

Jan. 24, 1979 [JP] Japan .................................. 54-7375
Mar. 12, 1979 [JP] Japan .................................. 54-28454

[51] Int. Cl.³ .......................................... H04M 7/18
[52] U.S. Cl. .................................. 358/93; 358/182; 358/183; 358/185; 434/94; 434/371
[58] Field of Search ................. 358/22, 127, 181, 180, 358/182, 183, 185, 93; 353/28, 77; 35/59; 434/94, 371

[56] References Cited

U.S. PATENT DOCUMENTS

| 2,061,378 | 11/1936 | Henze et al. | 35/59 |
| 2,061,378 | 11/1936 | Henze et al. | 434/94 |
| 2,309,390 | 1/1943 | Grossgnth et al. | 434/94 |
| 2,808,757 | 10/1957 | Scott | 434/371 |
| 2,921,387 | 1/1960 | Reeves | 434/94 |
| 3,120,066 | 2/1964 | Reeves | 434/94 |
| 3,339,453 | 9/1967 | Urich | 434/94 |
| 4,092,673 | 5/1978 | Adams | 358/183 |

Primary Examiner—Robert L. Richardson
Assistant Examiner—Edward L. Coles
Attorney, Agent, or Firm—Marvin H. Kleinberg

[57] ABSTRACT

A method and machine for trying on a hair form in image, in which a hair pattern portion is deleted from a face shape to be fitted by a hair pattern, and the face shape with the hair pattern thereon is displayed. In the machine, the hair pattern and the face shape with a mask for masking the hair pattern portion on it are arranged optically in symmetrical positions with respect to a half-mirror, and the face shape with the hair pattern thereon is taken through the half-mirror by a video camera. In the method, the hair pattern and the face shape are taken by the camera to obtain first and second signals by which the face shape with the hair pattern thereon is formed and then is displayed.

11 Claims, 5 Drawing Figures

METHOD AND MACHINE FOR TRYING ON A HAIR FORM IN IMAGE

BACKGROUND OF THE INVENTION

This invention relates to a method and machine for trying on a hair form in image prior to the arrangement.

A hair form is taken good care to be fixed up most suitably for features on the basis of clothing, fashion, seasons, events, and the like, after consideration of length and volume of the hair to be arranged by, especially, a girl or a woman.

In practice, however, when, after the hair form is arranged by a beauty specialist, the set of the hair is unsatisfactory, it is almost impossible to rearrange it, or, even if it is possible, it takes rather long time to do so. Thus, usually, the unsatisfactory hair set should be accepted unwillingly.

In a movie or a play, hairs of actresses and actors should be fixed up so as to fit to their characters or images. Accordingly, a method for checking a hair form prior to the arrangement has been expected.

SUMMARY OF THE INVENTION

It is an object of the present invention to provide a method for trying on a hair form in image, which is simple and reliable.

It is also an object of the present invention to provide a machine for trying on a hair form in image, which is simple and reliable.

According to the present invention there is provided a method for trying on a hair form in image, comprising photographing a face shape and a hair pattern by a video camera to obtain first and second signals, preparing a third signal for masking the hair pattern portion in the face shape by using the second signal, reducing the third signal from the first signal so as to mask the hair pattern portion in the face shape, adding the second signal to the first signal reduced so as to add the hair pattern to the hair pattern portion masked in the face shape, thereby obtaining a fourth signal for making the face shape with the hair pattern thereon, and displaying the face shape with the hair pattern thereon in a display means by using the fourth signal.

According to the present invention there is also provided a machine for trying on a hair form in image, comprising a video camera, a half silvered, semi-transparent mirror arranged in front of the video camera so that it may face a side direction at a certain angle with respect to a light axis of the video camera, a hair pattern and a screen having a face shape, with an opaque mask attached thereto, said mask reflecting no light and having the same shape as the hair pattern, which are symmetrically arranged in opposite sides of the half-mirror so that they may face the video camera so as to be photographed thereby via the half-mirror, and a display means, connected to the video camera, for displaying the face shape with the hair pattern thereon, wherein the hair pattern portion in the face is masked by the mask, and then the hair pattern is added to the hair pattern portion masked in the face shape, and wherein the face shape with the hair pattern thereon is taken through the half-mirror by the video camera.

BRIEF DESCRIPTION OF THE DRAWINGS

In order that the present invention may be better understood, preferred embodiments thereof will now be described with reference to the accompanying drawings, in which.

DESCRIPTION OF PREFERRED EMBODIMENTS

Figure 1:
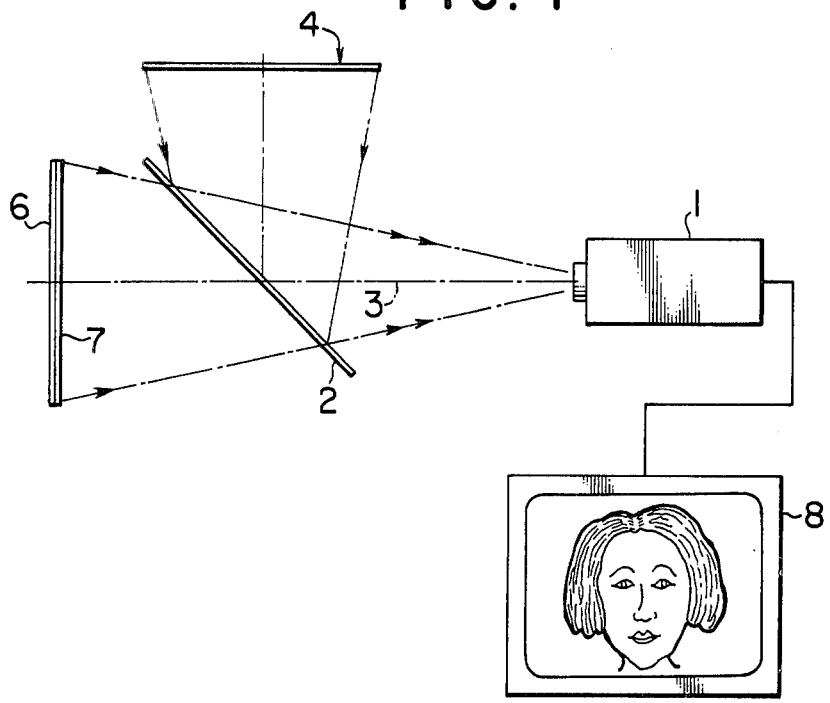
FIG. 1 is a schematic top view of a machine for trying on a hair form in image according to the present invention.

Referring now to the drawings, there is shown in FIG. 1 a video camera 1 of substantially conventional construction. In front of the camera 1 a half-mirror 2 is positioned vertically and faces a side direction at an angle of 45 degree with respect to an axis 3 of the light incident to the camera 1.

Figure 4:
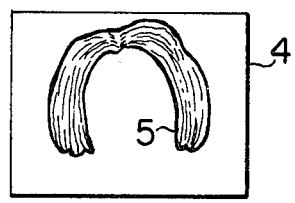
FIG. 4 shows a hair pattern plate to be used in the machine in FIG. 1.

A plain hair pattern plate 4, shown in FIG. 4, including a hair pattern 5 on its surface is positioned perpendicular skew to the light axis 3, in the upside in FIG. 1, so that it may be reflected by the half-mirror 2 and then be taken by the camera 1.

Figure 2:
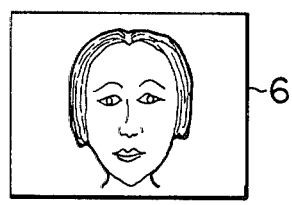
FIG. 2 shows a face picture plate to be used in the machine in FIG. 1.
Figure 3:
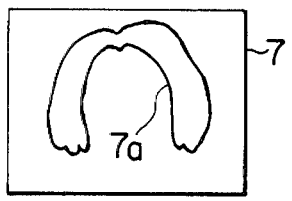
FIG. 3 shows a mask for a hair pattern, to be used in the machine in FIG. 1.

A face picture plate 6, shown in FIG. 2, having a face shape is so arranged perpendicular to the light axis 3 along it that it may be optically in a symmetric position of the hair pattern plate 4 with respect to the half-mirror 2. On the surface of the face picture plate 6 a transparent mask 7, shown in FIG. 3, including an opaque black masking pattern 7a which does not reflect any light and is the same shape as the hair pattern 5, is attached so that the masking pattern 7a may cover the hair of the face shape in the face picture plate 6.

In the arrangement described above, when illuminations (not shown) for the hair pattern plate 4 and the face picture plate 6 are properly adjusted, the masking pattern 7a attached on the face picture plate 6 is not reflected by the half-mirror 2, and thus the face overlapped with the hair pattern 5, in the face picture plate 6 is taken by the camera 1. Then the face including the hair pattern 5 is displayed in a display means 8 such as a cathode ray tube, or the like, which is connected to the camera 1.

From the above description, it is readily understood that the desired hair form can be formed by varying the hair pattern 5 of the hair pattern plate 4 and the masking pattern 7a of the mask 7.

Instead of the face picture plate 6, a face itself may be positioned behind the mask 7, while observing the face displayed in the display means 8 with the result of the same result described above. When the face picture to be attached to the plate 6 is small, the face picture enlarged in a real size may be projected to a screen covered by the mask 7, thereby obtaining the same result as described above.

The positions of the hair pattern plate 4 and the face picture plate 6 with the mask 7 shown in FIG. 1 may be interchangeable since they are positioned in the symmetrical positions with reference to the half-mirror 2.

Figure 5:
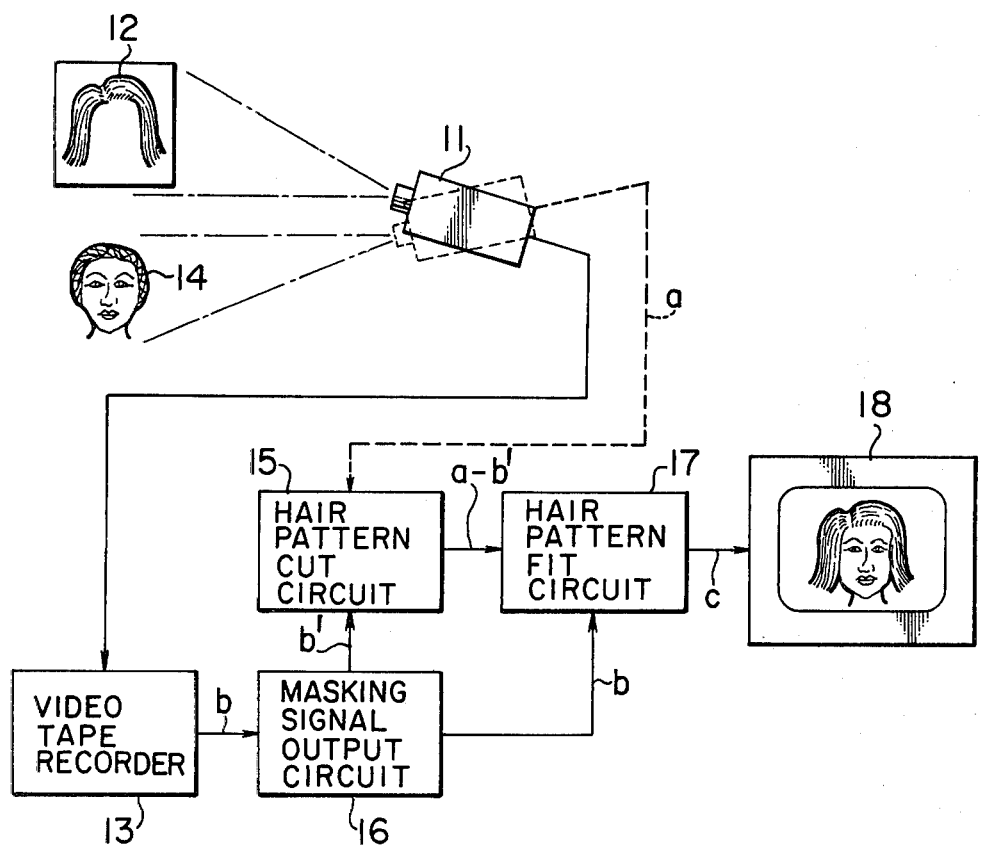
FIG. 5 is a schematic view of a system for explaining a method for trying on a hair form in image according to the present invention.

In FIG. 5 there is shown another embodiment of the present invention, in which the numeral 11 denotes a video camera. A plurality of hair patterns or wigs 12, one of which is shown in FIG. 5, are photographed by the camera 11, and are recorded in a video tape recorder 13. Then, a face 14 is photographed by the camera 11, and a picture signal a obtained is sent to a hair pattern cut circuit 15.

Then, a hair pattern signal b of one of the hair patterns 12 is selected and is applied in a stop mode from the video tape recorder 13 to a masking signal output circuit 16, in which a hair pattern masking signal b' is formed and is fed to the hair pattern cut circuit 15. In the hair pattern cut circuit 15, the portion corresponding to the selected hair pattern 12 is deleted from the face 14 according to the masking signal b'.

An output signal a-b' from the hair pattern cut circuit 15 and the hair pattern signal b from the masking signal output circuit 16 are sent to a hair pattern fit circuit 17, wherein the hair pattern signal b is added to the deleted portion deleted from the picture signal a by the masking signal b', thereby obtaining a composite signal c for making the face 14 with the selected hair pattern 12 thereon.

The composite signal c is sent to a display means 18 such as a cathode ray tube in order to display the face 14 having the desired hair pattern 12 thereon.

From the above description, it is readily understood that the desired hair form can be formed by selecting the one of the hair patterns recorded in the video tape recorder 13.

When the desired hair pattern is smaller than the natural hair of a face and head, the natural hair is diminished in size by covering it by a net before photographing the face.

In order to change the size of the hair pattern, the distance between the video camera 1 and the hair pattern 12 is changed, or a zoom-lens is used in the video camera 11. An anamorphic lens or optical system may be also used for obtaining a deformed hair pattern.

Although the present invention has been described with reference to a preferred embodiment thereof, however, various changes and modifications can be made by a person skilled in the art without departing from the scope of the present invention.

What is claimed is:

1. A method for trying on a hair form in image, comprising:
    photographing a face shape and a hair pattern by a video camera to obtain first and second signals respectively corresponding to face shape and hair pattern;
    preparing a third signal for masking the hair pattern portion in the face shape by using said second, hair pattern representing signal;
    combining said third signals with said first signal so as to mask effectively the hair pattern portion of the face shape;
    adding said second signal to the modified first signal so as to effectively add the hair pattern to partially masked face shape signal, thereby obtaining a fourth composite signal for making the face shape with the hair pattern thereon; and
    displaying the fourth signal to generate a face shape with the desired hair pattern thereon in a display means.

2. A method as claimed in claim 1, wherein said second signal representing the hair pattern is recorded in a video recorder before preparing the third signal.

3. A method as claimed in claim 2, wherein a plurality of second signals representing hair patterns are recorded in the video recorder, and one of them is selected from the video recorder in order to prepare the third signal.

4. A method as claimed in claim 1 or 3, wherein the video camera includes a zoom-lens.

5. A method as claimed in claim 1 or 3, wherein the video camera includes an anamorphic lens.

6. A machine for trying on a hair form in image, comprising:
    a video camera;
    a semi-transparent half silvered mirror arranged in front of said video camera so that it may face a side direction at a certain angle with respect to a light axis of said video camera;
    a hair pattern and a screen having a face shape, with an opaque mask attached thereto, said opaque mask reflecting no light and having substantially the same shape as said hair pattern, said pattern and said screen being symmetrically arranged on opposite sides of said half silvered mirror so that they are presented to said video camera so as to be photographed thereby via said half silvered mirror; and
    a display means, connected to said video camera, for displaying the face shape with the hair pattern optically combined therewith,
    wherein the hair pattern portion in said face shape is masked by the mask, and then said hair pattern is optically added to the hair pattern portion masked in said face shape, and wherein the face shape with the hair pattern combined therewith is presented through said half silvered mirror to said video camera.

7. A machine as claimed in claim 6, wherein said half silvered mirror faces a side direction at an angle of 45 degrees with respect to the light axis of said video camera.

8. A machine as claimed in claim 6 wherein said hair pattern is reflected by said half silvered mirror, and said face shape masked by the mask is taken through said half silvered mirror by said video camera.

9. A machine as claimed in claim 6, wherein said face shape masked by the mask is reflected by said half silvered mirror, and said hair pattern is taken through said half silvered mirror by said video camera.

10. A machine as claimed in claim 8, wherein the face shape is projected to said screen.

11. A machine as claimed in claim 9, wherein the face shape is projected to said screen.

* * * * *